United States Patent
Vasic

(10) Patent No.: US 8,496,778 B2
(45) Date of Patent: Jul. 30, 2013

(54) METHOD FOR MANUFACTURING AN ABSORBENT ARTICLE

(75) Inventor: Dragorad Vasic, Bollebygd (SE)

(73) Assignee: SCA Hygiene Products AB, Gothenburg (SE)

( * ) Notice: Subject to any disclaimer, the term of this patent is extended or adjusted under 35 U.S.C. 154(b) by 762 days.

(21) Appl. No.: 12/600,772

(22) PCT Filed: Jun. 26, 2007

(86) PCT No.: PCT/SE2007/000627
§ 371 (c)(1),
(2), (4) Date: Nov. 18, 2009

(87) PCT Pub. No.: WO2009/002235
PCT Pub. Date: Dec. 31, 2008

(65) Prior Publication Data
US 2010/0168706 A1    Jul. 1, 2010

(51) Int. Cl.
*B32B 37/00* (2006.01)
*B32B 37/02* (2006.01)
*B32B 38/00* (2006.01)
*B32B 38/04* (2006.01)

(52) U.S. Cl.
USPC ........... 156/253; 156/250; 156/252; 156/256; 156/267; 156/269; 156/270; 156/271

(58) Field of Classification Search
USPC ................. 156/250, 252, 253, 256, 267, 269, 156/270, 271
See application file for complete search history.

(56) References Cited

U.S. PATENT DOCUMENTS

| 4,940,464 | A | 7/1990 | Van Gompel et al. |
| 5,529,830 | A | 6/1996 | Dutta et al. |
| 5,540,796 | A | 7/1996 | Fries |
| 5,804,021 | A | 9/1998 | Abuto et al. |
| 8,216,414 | B2 * | 7/2012 | Hornung et al. ............... 156/259 |
| 2002/0052584 | A1 | 5/2002 | Forgar |
| 2003/0105446 | A1 | 6/2003 | Hutson et al. |
| 2003/0226862 | A1 | 12/2003 | Vogt et al. |
| 2004/0231765 | A1 | 11/2004 | Anflo et al. |
| 2005/0256495 | A1 | 11/2005 | Schlinz et al. |
| 2006/0266467 | A1 | 11/2006 | Mlinar |
| 2008/0009817 | A1 * | 1/2008 | Norrby ....................... 604/385.3 |
| 2009/0326503 | A1 * | 12/2009 | Lakso et al. ............. 604/385.23 |

FOREIGN PATENT DOCUMENTS

| DE | 19813334 A1 | 9/1999 |
| EP | 0 432 763 A1 | 6/1991 |

(Continued)

OTHER PUBLICATIONS

International Search Report for PCT/SE2007/000627, mailed Mar. 5, 2008.

(Continued)

*Primary Examiner* — Mark A Osele
*Assistant Examiner* — Christopher C Caillouet
(74) *Attorney, Agent, or Firm* — Buchanan Ingersoll & Rooney PC

(57) ABSTRACT

A method of manufacturing absorbent articles in which first and second stabilizing strips confer stability during the manufacturing process by controlling the position of side panels with respect to absorbent structures. In the thus manufactured articles, material of the stabilizing strips remain on the side panels to provide a region of material having consistent properties.

17 Claims, 4 Drawing Sheets

FOREIGN PATENT DOCUMENTS

| | | |
|---|---|---|
| EP | 1 035 818 B1 | 4/2002 |
| WO | WO 95/04654 A1 | 2/1995 |
| WO | WO 95/29810 A1 | 11/1995 |
| WO | WO 95/32093 A1 | 11/1995 |
| WO | WO 96/03952 A1 | 2/1996 |
| WO | WO 03/047488 A1 | 6/2003 |
| WO | WO 03/082168 A1 | 10/2003 |

OTHER PUBLICATIONS

Written Opinion of the International Searching Authority for PCT/SE2007/000627, mailed Mar. 5, 2008.

Decision on Patent Grant issued in RU 2010118317 dated May 12, 2012.

* cited by examiner

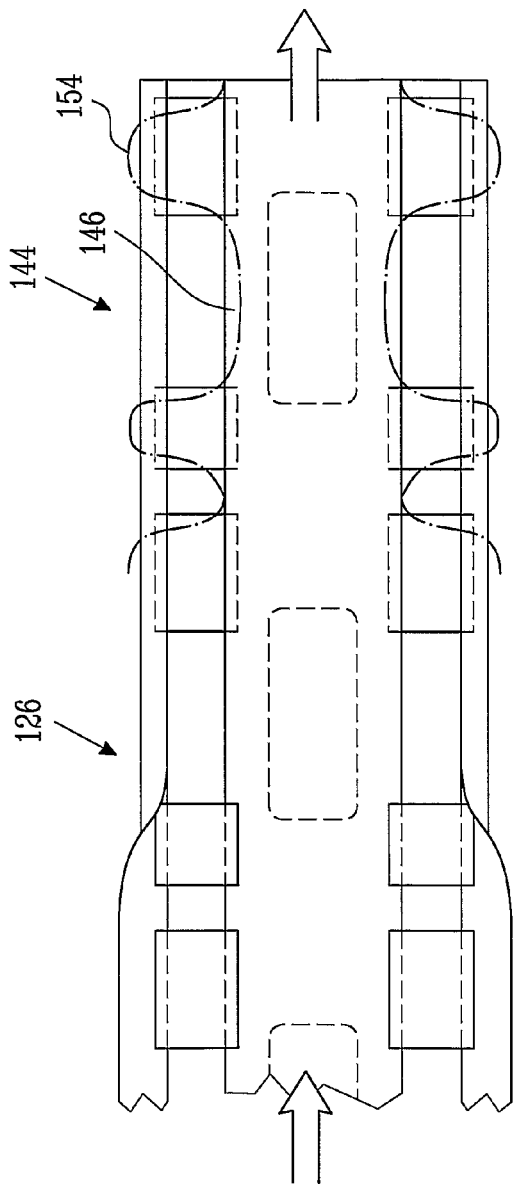
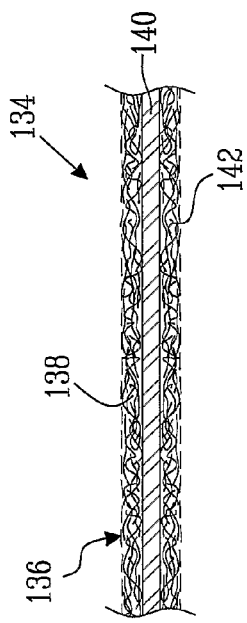

METHOD FOR MANUFACTURING AN ABSORBENT ARTICLE

TECHNICAL FIELD

The present invention relates to a method for manufacturing an absorbent article such as a disposable diaper, and to an absorbent article which may be made by such method.

BACKGROUND OF THE INVENTION

Production of absorbent articles such as baby diapers, adult incontinence diapers and belted diapers is performed at high speed. Due to the relatively low basis weight of materials used in the construction of such products, measures have to be taken to prevent the materials from lifting and/or fluttering during their passage through air. For continuous webs, such as the backsheet and topsheet materials, lifting and fluttering can be controlled by maintaining the webs under tension. However, many contemporary absorbent articles comprise side panels in addition to the topsheet and backsheet materials. Such side panels are used to provide the absorbent article with a transverse extension sufficient to allow the article to be fastened around the waist of a user. Although, during production, a continuous web of side panel material could be united with the continuous webs of backsheet and topsheet materials and thereby kept under tension, the side panel material in the crotch region has to be removed to create the finished product. Since the side panel material is often advantageously an elastic material, such a production technique, whilst addressing the problems of lifting and fluttering, results in uneconomic utilisation of material.

In order for absorbent articles to be secured around the waist of a wearer, it is necessary to provide the article with a fastening system. Contemporary fastening systems utilise a fastening tab secured to rear side panels. Particularly for articles having elasticised side panels, measures have to be taken to ensure that the fastening tabs are adequately affixed to the side panels. Such measures include deadening the elastic properties of the elasticised material in the region at which the fastening tape is to be secured to the side panel. Furthermore, since the fastening tab is normally directly attached to the side panel, compatibility of the materials is required.

A process for assembling elasticised side panels, or "ear portions", is described in WP-A-96/03952. According to its abstract, the process involves attaching at least one first fastener to a first web of side panel material and at least one second fastener to a second web of side panel material. A web of bridge material is provided with first and second side edge regions. The first web of side panel material is attached to the first side edge region of the web of bridge material, and the second web of side panel material is attached to the second side edge of the web of bridge material. The second web of side panel material is arranged to provide a cross-directional alignment between at least one corresponding, laterally opposed pair of the first and second fasteners. The web of bridge material and the first and second webs of side panel material are divided to provide at least one composite bridge assembly having a bridge member interconnecting a laterally opposed pair of first and second side panel members. The composite bridge assembly is secured to an appointed article web with the first and second side panels of the laterally opposed pair of side panel members located at opposite side regions of the article web.

In spite of the various known ways for integrating side panels and fasteners in absorbent articles, there remains a need for a method of producing an absorbent article in which the utilisation of side panel material is optimised at the same time that attachment of fastening tabs is facilitated.

SUMMARY OF THE INVENTION

The present invention addresses the above-identified need. Particularly, it provides a method for manufacturing absorbent articles, the method comprising the steps of:

providing a web of backsheet material, said web extending in a longitudinal direction about a longitudinal axis dividing the web into a first lateral half and a second lateral half, said first lateral half comprising a first lateral margin and said second lateral half comprising a second lateral margin;

sequentially applying absorbent structures to said web of backsheet material such that adjacent absorbent structures are spaced apart in said longitudinal direction;

providing a first stabilizing strip of predetermined width substantially parallel to said longitudinal axis, said first stabilizing strip being spaced from said first lateral margin in a transverse direction away from said longitudinal axis;

providing a second stabilizing strip of predetermined width substantially parallel to said longitudinal axis, said second stabilizing strip being spaced from said second lateral margin in a transverse direction away from said longitudinal axis;

with respect to each absorbent structure, providing a first side panel having a first major surface and a second major surface;

applying said first major surface of said first side panel to said first lateral margin of said web such that said first major surface contacts said first stabilizing strip;

with respect to each absorbent structure, providing a second side panel having a first major surface and a second major surface, and applying said first major surface of said second side panel to said second lateral margin of said web such that said first major surface contacts said second stabilizing strip, to thereby form an initial united structure.

In accordance with the invention, due to the provision of first and second stabilizing strips, opposite end regions of the first and second side panels are held in place during production without the need for a continuous web of side panel material or material bridging the side panels. In addition, the region of the first and second stabilizing strips to which the side panels are affixed may be retained on the finished article to provide a suitable surface to which to attach fastening tabs.

Accordingly, it is a further object of the invention to provide an absorbent article which is intended to be worn around the waist of a user, which article presents side panels having a suitable surface on which to attach fastening tabs.

This object is achieved in accordance with the present invention by an absorbent article intended to be worn around the waist of a user, the article comprising a chassis comprising a topsheet, a backsheet and an absorbent structure therebetween. The chassis extends in a longitudinal direction about a longitudinal axis dividing the chassis into a first lateral half and a second lateral half. The first lateral half comprises a first lateral margin and the second lateral half comprises a second lateral margin. The chassis also extends in a transverse direction about a transverse axis which divides the chassis into a first end and a second end, with the chassis being delimited by a periphery comprising a first end edge at the first end and a second end edge at the second end. The first and second end edges extend substantially parallel to the transverse axis. The periphery further comprises a first lateral edge of the first lateral margin and a second lateral edge of the second lateral margin. The first and second lateral margins have a first end region extending from the first end edge, a second end region extending from the second end edge and a central region extending between said first and second end regions. The article further comprises a first side panel extending from the first lateral edge in the first end region, a second side panel extending from the second lateral edge in the first end region, a third side panel extending from the first lateral edge in the second end region and a fourth side panel extending from the second lateral edge in the second end region. Each panel has a first major surface and a second major surface and a longitudinally extending peripheral margin having a length dimension. A strip of essentially non-elastic material extends the entire length dimension along said longitudinally extending peripheral margin of at least one transversely opposed pair of said side panels.

In this manner, a fastening tab can be readily attached to the strip of essentially non-elastic material.

Further advantageous embodiments of the garment and its method of manufacture are detailed in the dependent claims appended hereto.

BRIEF DESCRIPTION OF THE DRAWINGS

The invention will be described in greater detail in the following by way of example only with reference to various non-limiting embodiments as depicted in the annexed drawings, in which

FIG. 3 is a schematic plan view of the manufacturing process at the region denoted by arrow B in FIG. 1;

FIG. 5 is a schematic cross-sectional view of an elastic material suitable for use in first and second side panels of the absorbent article according to the invention.

DETAILED DESCRIPTION OF THE INVENTION

Figure 4:
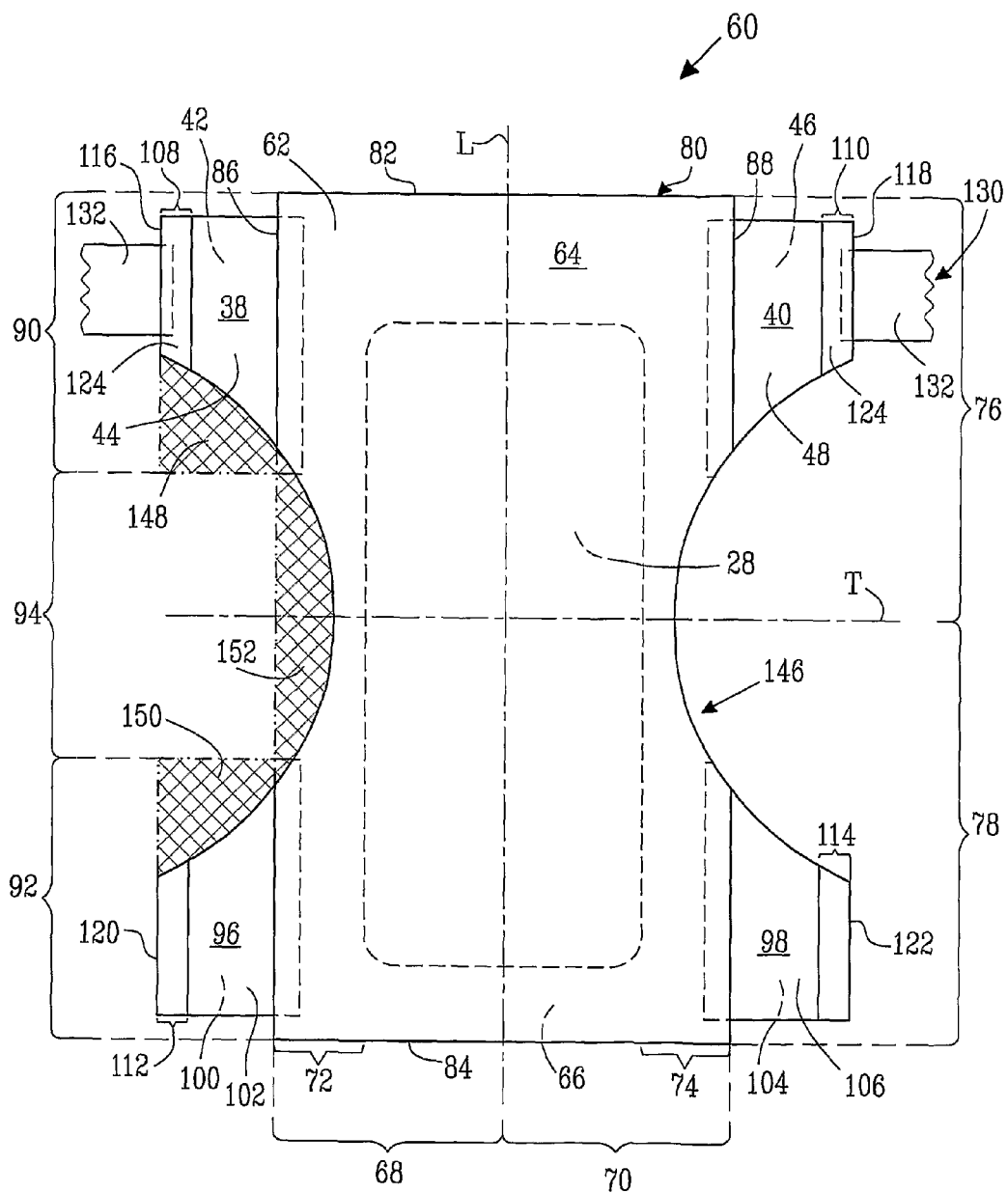
FIG. 4 is a schematic view of an absorbent article according to the present invention in a laid-flat, uncontracted state.

The invention will be described in further detail in the following with reference to the drawings in which reference number 10 generally denotes a manufacturing process utilising the method in accordance with the present invention to produce an absorbent article 60 as depicted in FIG. 4.

Figure 1:
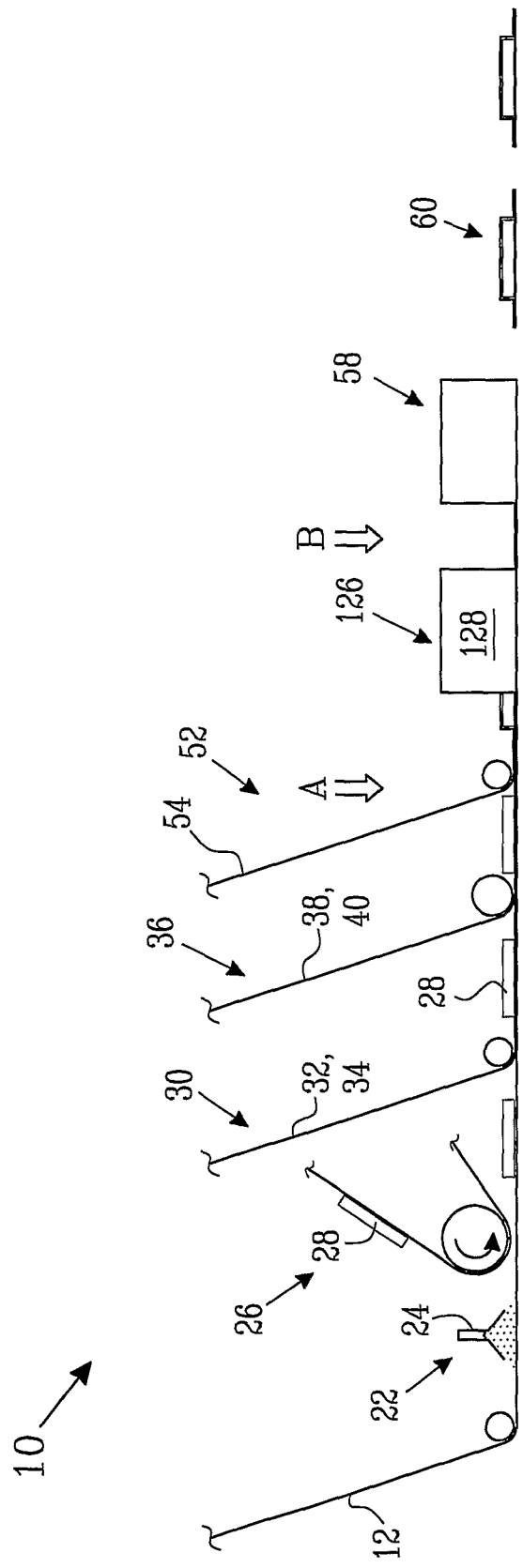
FIG. 1 is a schematic view of a manufacturing process utilising the method of the present invention.

With particular reference to FIG. 1, the method includes providing a web 12 of backsheet material. The backsheet material is advantageously a liquid impervious material such as a thin plastic film, e.g. a polyethylene or polypropylene film, a nonwoven material coated with a liquid impervious material, a hydrophobic nonwoven material which resists liquid penetration, or a laminate comprising plastic films and nonwoven materials. The backsheet material may be breathable. Examples of suitable breathable materials are porous polymeric films, nonwoven laminates from spunbond and meltblown layers, laminates from porous polymeric films and nonwovens.

Figure 2:
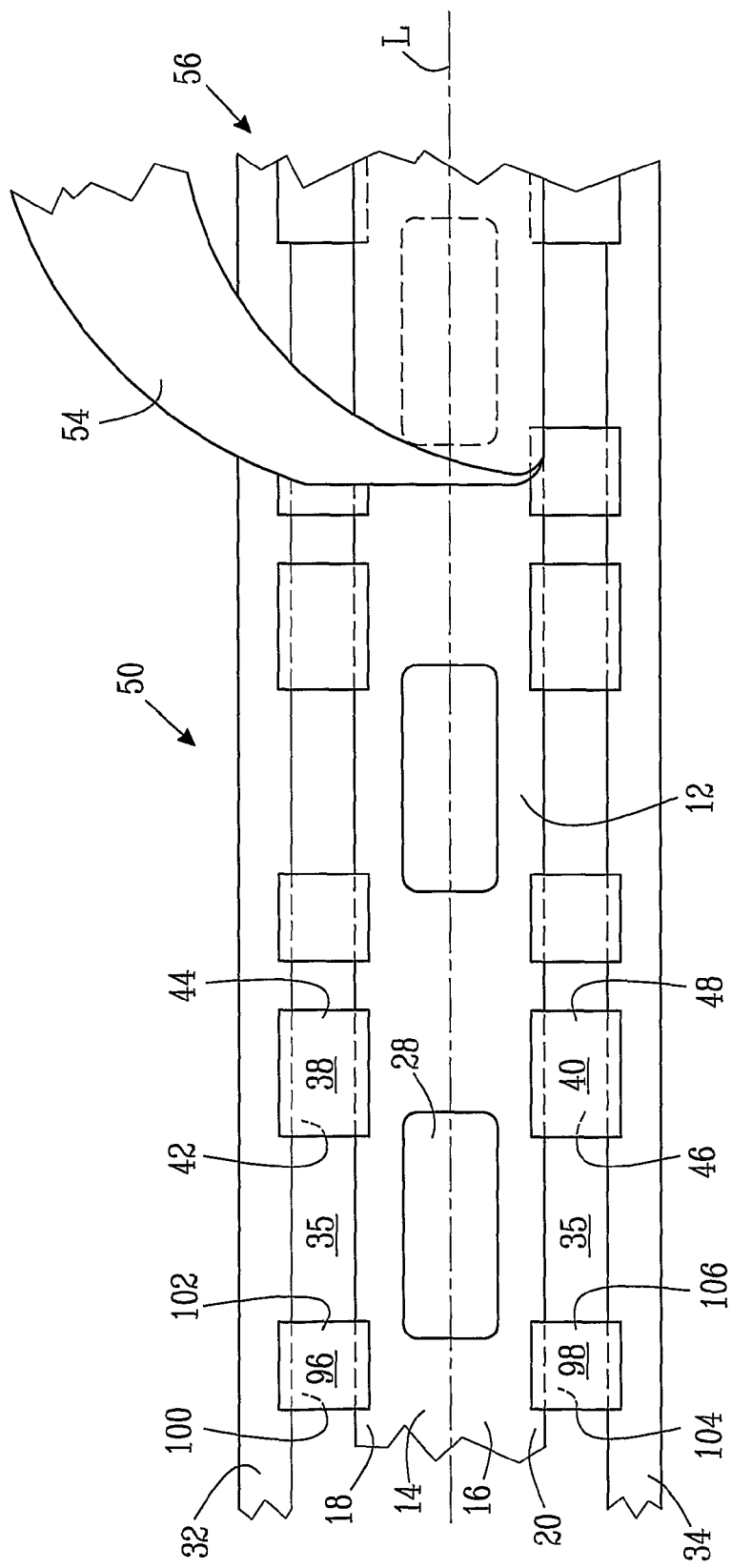
FIG. 2 is a schematic plan view of the manufacturing process at the region denoted by arrow A in FIG. 1.

The web 12 of backsheet material may be unwound from a not-shown reel and brought to run in a substantially horizontal plane such that the web extends in a longitudinal direction about a longitudinal axis L which divides the web into a first lateral half 14 and a second lateral half 16 (see FIG. 2). The first lateral half 14 has a first lateral margin 18 and the second lateral half 16 has a second lateral margin 20. The web 12 is oriented during the manufacturing process such that its upwardly facing surface corresponds to the inwardly directed surface of the final product and its downwardly facing surface corresponds to the outwardly directed surface of the final product.

At a first processing station, generally indicated by reference sign 22, adhesive may be applied to the upwardly facing surface of the web 12 of backsheet material by means of, for example, a hot-melt spraying apparatus 24. In a known manner, the adhesive may be spayed to form a uniform layer or may be applied in a pattern such as a spiral pattern.

At a second processing station, generally indicated by reference sign 26, absorbent structures 28 are sequentially applied to the web 12 of backsheet material. As is conventional, the absorbent structures are applied to the web so that the absorbent structures are spaced apart in the longitudinal direction. The spacing between absorbent structures corresponds to the length of the final product minus the length of the absorbent structure. The absorbent structures are held in place by the adhesive on the web 12 of backsheet material. Alternatively, each absorbent structure may be coated with adhesive on the side which is to contact the web of backsheet material.

The absorbent structures 28 may be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent body. It is also common to have absorbent bodies comprising layers of different material with different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent. The size and absorbent capacity of the absorbent structure may be varied to be suited for different uses such as for infants or for incontinent adults. The absorbent structures need not display a uniform thickness and may be thinner at one end.

At a third processing station, generally indicated by reference sign 30, a first and a second stabilizing strip 32, 34 are brought to run parallel to, and substantially coplanar with, the longitudinal axis L of the web 12 of backsheet material. As is most clearly derivable from FIG. 2, the first stabilizing strip 32 is spaced from the first lateral margin 18 of the web of backsheet material in a transverse direction away from the longitudinal axis L, and the second stabilizing strip 34 is spaced from the second lateral margin 20 in a similar manner. The spacing of the stabilizing strips from the respective lateral margins creates a gap 35 on either side of the web 12 of backsheet material. The size of the gap 35 will be dependent on the chosen geometry of the final product. For an open type infant's diaper, the gap 35 may be from about 3 cm to about 15 cm. For a belted product, the gap may be as large as about 80 cm. The stabilizing strips should be substantially inextensible and non-elastic, at least in their length direction, and may have a transverse dimension of between 2 cm and 8 cm, preferably about 4 cm, depending on the size of the final product. Materials useful for the stabilizing strips include nonwoven material, for example spunbond, meltblown, carded, hydroentangled, wetlaid, etc. Suitable nonwoven materials can be composed of natural fibers, such as woodpulp or cotton fibres, manmade fibres, such as polyester, polyethylene, polypropylene, viscose etc. or from a mixture of natural and manmade fibres. Such nonwoven material may have a basis weight of from about 30 g/m² to 70 g/m², preferably about 50 g/m². The stabilizing strips 32, 34 may be precoated with adhesive, for example any conventional pressure-sensitive adhesive.

At a fourth processing station, generally indicated by reference sign 36, a first and a second side panel 38, 40 are applied to the web 12 of backsheet material at a specific location with respect to an associated absorbent structure 28. Thus, since the first and second side panels 38, 40 are intended to form waist side panels in the final product, the side panels are positioned with respect to the absorbent structure such that they will form an extension of the rear waist region of the final product. With particular reference to FIG. 2, the first side panel 38 has a first major surface 42 and a second major surface 44. In a corresponding manner, the second side panel 40 has a first major surface 46 and a second major surface 48. At the fourth processing station 36, the first major surface 42 of the first side panel 38 is applied to the first lateral margin 18 of the web 12 of backsheet material such that the first major surface 42 also contacts the first stabilizing strip 32. In this manner, the gap 35 between the first stabilizing strip 32 and the web 14 is bridged by the first side panel 38. Similarly, the first major surface 46 of the second side panel 40 is applied to the second lateral margin 20 of the web 12 of backsheet material such that the first major surface 46 also contacts the second stabilizing strip 34 to thereby bridge the gap 35 between the second stabilizing strip and the web of backsheet material. With the first and second side panels applied in the above manner, the combination of web 12 of backsheet material, absorbent structures 28 and first and second side panels 38, 40 forms an initial united structure 50.

In a further embodiment of the invention, at a fifth processing station, generally denoted by reference number 52 in FIG. 1, a web 54 of topsheet material is applied to the initial absorbent structure 50 to form a subsequent united structure 56 (FIG. 2). The web 54 is liquid permeable and can consist of a nonwoven material, for example spunbond, meltblown, carded, hydroentangled, wetlaid, etc. Suitable nonwoven materials can be composed of natural fibers, such as wood-pulp or cotton fibres, manmade fibres, such as polyester, polyethylene, polypropylene, viscose etc. or from a mixture of natural and manmade fibres. The web 54 may further be composed of tow fibres, which may be bonded to each other in a bonding pattern, as e.g. disclosed in EP-A-1 035 818. Further examples of suitable topsheet web materials are porous foams, apertured plastic films etc. The materials suited as the topsheet web layer should be soft and non-irritating to the skin and intended to be readily penetrated by body fluid, e.g. urine or menstrual fluid.

The web 54 of topsheet material has an extension in the transverse direction corresponding essentially to that of the web 12 of backsheet material. As such, the portions of the second major surfaces 44, 48 of the side panels 38, 40 which contact the web 12 of backsheet material are covered by the web 54 of topsheet material to thereby sandwich these portions between the webs of backsheet and topsheet material.

In a further embodiment of the present invention, at a sixth processing station 58 the subsequent united structure 56 is severed in the transverse direction to form individual absorbent articles 60. The severing is arranged to take place at a location on the subsequent united structure 56 between adjacent absorbent structures 28 to thereby form an individual absorbent article 60 as generally illustrated in FIG. 4.

Thus, in accordance with the present invention, the absorbent article 60 comprises a chassis 62 comprising a topsheet 64 of a length of the web 54 of topsheet material, a backsheet 66 of a length of the web 12 of backsheet material and an absorbent structure 28 therebetween. The chassis 62 extends in a longitudinal direction about a longitudinal axis L dividing the chassis into a first lateral half 68 and a second lateral half 70. The first lateral half 68 comprises a first lateral margin 72 and the second lateral half 70 comprises a second lateral margin 74. The chassis 62 further extends in a transverse direction about a transverse axis T dividing the chassis into a first end 76 and a second end 78. The chassis is delimited by a periphery 80 comprising a first end edge 82 at the first end 76 and a second end edge 84 at the second end 78. The first and second end edges 82, 84 extend substantially parallel to the transverse axis T. The periphery 80 further comprises a first lateral edge 86 of the first lateral margin 72 and a second lateral edge 88 of the second lateral margin 74. The first and second lateral margins 72, 74 have a first end region 90 extending from the first end edge 82, a second end region 92 extending from the second end edge 84 and a central region 94 extending between the first and second end regions.

The article 60 further comprises a first side panel 38 extending from the first lateral edge 86 in the first end region 90 and a second side panel 40 extending from the second lateral edge 88 in the first end region 90. The first and second side panels are thus constituted by the first and second side panels 38, 40 applied at the fourth processing station 36 in the above-described manufacturing process.

The article 60 further has a third side panel 96 extending from the first lateral edge 86 in the second end region 92 and a fourth side panel 98 extending from the second lateral edge 88 in said second end region 92. Depending on the desired relative properties of the pairs of first and second and third and fourth side panels, the third and fourth side panels 96, 98 may also be constituted by the first and second side panels 38, 40 applied at the fourth processing station 36 in the manufacturing process, with the severing at the sixth processing station 58 being carried out such that it divides the side panels in the transverse direction to thereby form the four side panels. When the first and second side panels 38, 40 applied at the fourth processing station are of identical material, so too will the third and fourth side panels 96, 98 be.

Should it be desired to have third and fourth side panels 96, 98 of a material different to that of the first and second side panels 38, 40, or to have them positioned at a location on the absorbent article 60 remote from the second end edge 84, the manufacturing method further includes the steps of (see FIG. 2), with respect to each absorbent structure 28, providing a third side panel 96 having a first major surface 100 and a second major surface 102; applying the first major surface of the third side panel to the first lateral margin 18 of the web 12 of backsheet material at a distance from the first side panel 38 such that the first major surface 100 contacts the first stabilizing strip 32; with respect to each absorbent structure, providing a fourth side panel 98 having a first major surface 104 and a second major surface 106, and applying the first major surface 104 of the fourth side panel 98 to the second lateral margin 20 of the web 12 of backsheet material at a distance from the second side panel 40 such that the first major surface 104 contacts the second stabilizing strip 34.

With continued reference to FIG. 4, each side panel 38, 40, 96, 98 therefore has a first major surface 42, 46, 100, 104 and a second major surface 44, 48, 102, 106 and a longitudinally extending peripheral margin 108, 110, 112, 114 having a length dimension 116, 118, 120, 122, respectively. In accordance with the invention, a strip 124 of essentially non-elastic material extends the entire length dimension 116, 118, 120, 122 along the longitudinally extending peripheral margin of at least one transversely opposed pair of the side panels. The strip 124 of essentially non-elastic material is constituted by longitudinal sections of the stabilizing strips 32, 34 used in the above-described method.

In one embodiment of the invention, the strip 124 of essentially non-elastic material extends the entire length dimension of the first and second side panels 38, 40. In a second embodiment, the strip 124 also extends the entire length dimension of said third and fourth side panels 96, 98.

The strip 124 of essentially non-elastic material may be affixed to solely the first major surface 42, 46, 100, 104 of each side panel 38, 40, 96, 98, or it may be affixed to both the first major surface and the second major surface 44, 48, 102, 106 of each side panel 38, 40, 96, 98. In the latter case, the method for manufacturing the article includes a seventh processing station 126 located upstream of the sixth processing station 58 (see FIG. 1). The seventh processing station comprises folding equipment 128 to fold the first and second stabilizing strips 32, 34 over the lateral edges of the side panels such that the stabilizing strips come into contact with the second major surface 44, 48 of the side panels. This step of folding the first and second stabilizing strips 32, 34 over the lateral edges of the side panels is schematically illustrated in FIG. 3.

Thus, in a preferred embodiment of the present invention, the method includes applying the first major surface 42 of the first side panel 38 to the first lateral margin 18 of the web 12 of backsheet material such that the first major surface contacts only a portion of the width of the first stabilizing strip 32, applying the first major surface 46 of the second side panel 40 to the second lateral margin 20 of the web 12 such that the first major surface contacts only a portion of the width of the second stabilizing strip 34, and folding the first and second stabilizing strips 32, 34 such that the first stabilizing strip also contacts the second major surface 44 of the first side panel and the second stabilizing strip 34 also contacts the second major surface 48 of the second side panel 40.

Similarly, when distinct third and fourth side panels are applied in the method of the invention, the method may further include applying the first major surface 100 of the third side panel 96 to the first lateral margin 18 of the web 12 of backsheet material such that the first major surface contacts only a portion of the width of the first stabilizing strip 32, applying the first major surface 104 of the fourth side panel 98 to the second lateral margin 20 of the web 12 such that the first major surface contacts only a portion of the width of the second stabilizing strip 34, and folding the first and second stabilizing strips to cause the first stabilizing strip 32 to also contact the second major surface 102 of the third side panel 96 and the second stabilizing strip 34 to also contact the second major surface 106 of the fourth side panel 98.

Whether the stabilizing strips 32, 34 contact only the first major surface of the side panels or both the first and second major surfaces, the absorbent article 60 will nevertheless exhibit a strip 124 of essentially non-elastic material extending the entire length dimension along the peripheral margin of at least one transversely opposed pair of side panels. Such a region of non-elastic material is convenient for attaching a fastening means 130 to the article 60 in a secure manner, particularly if the side panel has elastic properties. Advantageously, the fastening means 130 is attached to the strip 124 of essentially non-elastic material on the first and second side panels 38, 40. For an open-type diaper, the fastening means may constituted by a fastening tab 132. Alternatively, for a closed diaper of the pull-on type, the fastening means 130 is constituted by a first seal between the first and third side panels 38, 96 and a second seal between the second and fourth side panels 40, 98 to thereby form a pants-type garment. Such a seal may be formed by ultrasonic heat treatment of portions of the strip 124 lying against the second major surfaces of the respective side panels.

For reasons of improved fit and comfort, the first and second side panels 38, 40 may exhibit elastic properties at least in the transverse direction. The first and second side panels may comprise various suitable materials. As shown in FIG. 5, in one embodiment the material 134 is an elastic web material in the form of an elastic laminate 136 comprising a first layer 138 of fibrous material and an elastic film layer 140. The elastic laminate may optionally include a second layer 142 of fibrous material, with the elastic film layer being located between the first and second layers of fibrous material. However it is to be understood that other types of elastic web materials may be used, such as elastic nonwoven materials, nonwoven materials which per se are inelastic, but which have been elastified by suitable means, etc. The elastic web materials may comprise one layer or two or more layers that have been laminated.

In the elastic laminate 136 shown and described below it is preferred that the first and second layers of fibrous material 138, 142 are chosen so that they, in combination with the inner elastic film layer 140, give the material high resistance to puncture. They also provide a soft and cloth-like feel to the laminate. Examples of suitable materials are carded webs and spunbond materials. The basis weight of the fibrous material layers should be between 10 and 35 $g/m^2$, preferably between 12 and 30 $g/m^2$, more preferably between 15 and 25 $g/m^2$. Examples of suitable polymers used in the fibrous materials are polyethylene, polyesters, polypropylene and other polyolefin homopolymers and copolymers. Natural fibres, for example cotton, may also be used as long as they provide the required properties. A mixture of polymers can contribute to a higher flexibility of the nonwoven layer, and in this way, give the nonwoven material a higher elongation at maximum load. A mixture of polyethylene and polypropylene polymers has proved to provide good results in this respect. A mixture of fibers of different polymers is also possible.

The elastic film layer 140 may be constituted by an apertured elastic film having a basis weight between 20 and 80 $g/m^2$, preferably between 20 and 60 $g/m^2$. The film may be of any suitable elastic polymer, natural or synthetic. Some examples of suitable materials for the elastic film are low crystallinity polyethylenes, metallocene-catalyzed low crystallinity polyethylene, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable film is an apertured three-layer elastomeric film of PE-SEBS-PE.

For i.a. reasons of comfort, it is advantageous if the total basis weight of the laminate can be kept low. Thus, although a total basis weight of about 150 $g/m^2$ is acceptable, a total basis weight of 100 $g/m^2$ or less, for example no more than 90 $g/m^2$, is preferred.

The elastic laminate 136 may be manufactured according to the method disclosed in WO 03/047488, wherein one spunbond layer 138 is applied to the film 140 in a tacky state and will thus bond to the film layer, while the other spunbond layer 142 is adhesively laminated to the film layer 140, using for example a pressure sensitive hot melt adhesive.

The method disclosed in WO 03/047488 involves stretching of the laminate above the point of failure of the fibrous material, so that the non-elastic layers break completely.

Therefore, as described in WO 03/047488, the elongation of the laminate is not limited by the stretch modulus of the non-elastic material.

Elasticity in both the longitudinal direction and the transverse direction may be imparted to the laminate in the manner disclosed in, for example, WO-A-95/04654.

To provide additional wearer comfort, the elastic laminate 136 may be breathable and have a Water Vapour Transmission Rate according to ASTM E96-00 of at least 1500 g/m²-24 h, preferably at least 3000 g/m²-24 h.

Bi-directionally elastically extensible material which may be adapted for use in the present invention is described in the art. Examples include that which is disclosed in US-A1-2003/0105446, WO-A-95/29810, EP-A-0 432 763 and WO-A-95/32093, the contents of which are hereby incorporated by reference.

As is derivable from FIG. 5, the elastic material 134 of the first and second side panels 38, 40 may be substantially homogenous. By "substantially homogenous" it is meant that, irrespective of where on the elastic material samples of 25 mm² surface area are taken through the thickness of the material, their compositions will be effectively identical, i.e. it should not be possible to identify a particular area having a composition which differs from any other area. As a result, the material will display substantially the same properties irrespective of where on the material sample measurements are made. In one embodiment of the invention, the first and second side panels 38, 40 are made entirely of elastic material.

When the third and fourth side panels 96, 98 are made of a material different to that of the first and second side panels, the material of the third and fourth side panels may, for cost reasons, be essentially non-elastic.

To reduce the risk of the garment "bunching" in use, it may be advantageous if the chassis 60 is also substantially non-elastic.

The absorbent article illustrated in FIG. 4 may further comprise so-called standing gathers (not shown). As is known per se, by providing the free end of the gathers with elastic threads, barriers to the transmission of bodily waste in the transverse direction are created. The material of the standing gathers may be the same as for the topsheet layer 64 or it may be different. Purely by way of example, the topsheet may be a spunbond material and the standing gathers may be constituted by a meltblow material. When standing gathers are to be incorporated in the absorbent article, this is done in a manner known per se at a (not shown) processing station upstream of the sixth processing station 58 at which the subsequent united structure 56 is severed.

In order for the absorbent article 60 to be serviceable, the material constituted by the first and second stabilizing strips 32, 34, which extends between the first and third side panels 38, 96 and the second and fourth side panels 40, 98 has to be removed. This removal of stabilizing strip material may be effected at an eighth processing station 144 (see FIG. 3) located between the seventh processing station 126 and the sixth processing station 58. In one embodiment of the invention, the removal of the material occurs during formation of leg openings 146 by removal of material from at least one transversely opposed pair of side panels 38, 40; 96, 98. Thus, in FIG. 4, material 148 may be removed from the first and second side panels 38, 40 and/or material 150 may be removed from the third and fourth side panels 96, 98. In order to remove the material constituted by the first and second stabilizing strips 32, 34, which extends between the first and third side panels 38, 96 and the second and fourth side panels 40, 98, the material 148, 150 removed from the side panels should extend to the transverse edges of the side panels.

In a further embodiment of the invention, the formation of the leg openings 146 also includes removal of topsheet material and backsheet material, as indicated by reference number 152. Preferably, the formation of the leg openings is effected in one cutting operation in which the material 148, 150 and 152 is removed to thereby create a continuous curved leg opening. A suitable cutting path for a cutter is schematically illustrated in FIG. 3 and denoted by reference number 154.

Although the method and article described above relate to either an open or closed type diaper, in a further aspect of the present invention, the first and second side panels 38, 40 may be constituted by belt halves of a belted absorbent article. Thus, for such an article, suitably folded belt halves are applied to the web 12 of backsheet material at the fourth processing station 36 to bridge the gap 35 between the first and second stabilizing strips. The belt halves may be folded such that the first and second stabilizing strips form the outer edges of the belt halves, or provide regions of material transversely inwardly of the outer edges.

The invention has been described in the above by way of example only and various modifications will be apparent to the skilled person. For example, although a method has been described in which adhesive is applied to the web 12 of backsheet material, it is to be understood that adhesive may instead be applied to the components which are to come into contact with the web, such as the absorbent structures 28 and the side panels. Accordingly, it is to be understood that the scope and limitations of the invention are defined solely by the appended claims.

The invention claimed is:

1. A method for manufacturing absorbent articles, the method comprising the steps of:
    providing a web of backsheet material, said web extending in a longitudinal direction about a longitudinal axis dividing the web into a first lateral half and a second lateral half, said first lateral half comprising a first lateral margin and said second lateral half comprising a second lateral margin;
    sequentially applying absorbent structures to said web of backsheet material such that adjacent absorbent structures are spaced apart in said longitudinal direction;
    providing a first stabilizing strip of predetermined width substantially parallel to said longitudinal axis, said first stabilizing strip being spaced from said first lateral margin in a transverse direction away from said longitudinal axis;
    providing a second stabilizing strip of predetermined width substantially parallel to said longitudinal axis, said second stabilizing strip being spaced from said second lateral margin in a transverse direction away from said longitudinal axis;
    with respect to each absorbent structure, providing a first side panel having a first major surface and a second major surface;
    applying said first major surface of said first side panel to said first lateral margin of said web such that said first major surface contacts said first stabilizing strip;
    with respect to each absorbent structure, providing a second side panel having a first major surface and a second major surface, and
    applying said first major surface of said second side panel to said second lateral margin of said web such that said first major surface contacts said second stabilizing strip, to thereby form an initial structure.

2. The method as claimed in claim 1, further comprising the steps of:
  providing a web of topsheet material, and
  applying said web of topsheet material to said initial structure to thereby form a subsequent structure.

3. The method as claimed in claim 2, further comprising the step of:
  severing said subsequent structure in said transverse direction to thereby divide said first and second side panels.

4. The method as claimed in claim 3, wherein said step of severing said subsequent structure is effected at a location between adjacent absorbent structures.

5. The method as claimed in claim 4, wherein prior to severing said subsequent structure, material constituting said first and second stabilizing strips extending between adjacent side panels is removed.

6. The method as claimed in claim 5, wherein removal of said material occurs during formation of leg openings by removal of material from at least one transversely opposed pair of side panels.

7. The method as claimed in claim 6, wherein said formation of leg openings includes removal of topsheet material and backsheet material.

8. The method as claimed in claim 1, comprising the steps of:
  with respect to each absorbent structure, providing a third side panel having a first major surface and a second major surface;
  applying said first major surface of said third side panel to said first lateral margin of said web at a distance from said first side panel such that said first major surface contacts said first stabilizing strip;
  with respect to each absorbent structure, providing a fourth side panel having a first major surface and a second major surface, and
  applying said first major surface of said fourth side panel to said second lateral margin of said web at a distance from said second side panel such that said first major surface contacts said second stabilizing strip.

9. The method as claimed in claim 8, wherein said first and second side panels are substantially identical, and said third and fourth side panels are substantially identical.

10. The method as claimed in claim 9, wherein said first and second side panels are different from said third and fourth side panels.

11. The method as claimed in claim 8, wherein
  said first major surface of said first side panel is applied to said first lateral margin of said web such that said first major surface contacts only a portion of the width of said first stabilizing strip;
  said first major surface of said second side panel to said second lateral margin of said web such that said first major surface contacts only a portion of the width of said second stabilizing strip,
  said first major surface of said third side panel is applied to said first lateral margin of said web such that said first major surface contacts only a portion of the width of said first stabilizing strip;
  said first major surface of said fourth side panel to said second lateral margin of said web such that said first major surface contacts only a portion of the width of said second stabilizing strip,
  the method further comprising the step of folding said first and second stabilizing strips such that said first stabilizing strip also contacts said second major surface of said first side panel and said second stabilizing strip also contacts said second major surface of said second side panel,
  in which the step of folding said first and second stabilizing strips causes said first stabilizing strip to also contact said second major surface of said third side panel and said second stabilizing strip to also contact said second major surface of said fourth side panel.

12. The method as claimed in claim 8, further comprising the step of:
  severing said subsequent structure in said transverse direction at a location along said web between said first and third and second and fourth side panels and between adjacent absorbent structures.

13. The method as claimed in claim 1, wherein said first and second side panels are substantially identical, and said third and fourth side panels are substantially identical.

14. The method as claimed in claim 1, wherein said first and second side panels are made from a material displaying elastic properties in at least the transverse direction.

15. The method as claimed in claim 1, wherein said first and second stabilizing strips are substantially inextensible and non-elastic at least in their length direction.

16. The method as claimed in claim 15, wherein said first and second stabilizing strips are made on nonwoven material having a basis weight of from about 30 $g/m^2$ to 70 $g/m^2$.

17. The method as claimed in claim 1, wherein
  said first major surface of said first side panel is applied to said first lateral margin of said web such that said first major surface contacts only a portion of the width of said first stabilizing strip;
  said first major surface of said second side panel to said second lateral margin of said web such that said first major surface contacts only a portion of the width of said second stabilizing strip,
  the method further comprising the step of folding said first and second stabilizing strips such that said first stabilizing strip also contacts said second major surface of said first side panel and said second stabilizing strip also contacts said second major surface of said second side panel.

* * * * *